United States Patent
Shi et al.

(10) Patent No.: US 12,286,647 B1
(45) Date of Patent: Apr. 29, 2025

(54) ESTABLISHMENT AND SUSPENSION ACCLIMATION OF CRFK ADHERENT CELL LINE, AND ITS APPLICATION

(71) Applicant: Taizhou Bioally Technology Co., Ltd., Jiangsu (CN)

(72) Inventors: Wenda Shi, Jiangsu (CN); Zhonghua Zhang, Jiangsu (CN); Hao Dong, Jiangsu (CN); Xiao Zhao, Jiangsu (CN); Zhihui Ji, Jiangsu (CN); Jihong Liu, Jiangsu (CN); Hongwei Wang, Jiangsu (CN)

(73) Assignee: Taizhou Bioally Technology Co., Ltd., Taizhou (CN)

( * ) Notice: Subject to any disclaimer, the term of this patent is extended or adjusted under 35 U.S.C. 154(b) by 0 days.

(21) Appl. No.: 18/801,895

(22) Filed: Aug. 13, 2024

(30) Foreign Application Priority Data

Oct. 19, 2023 (CN) .......................... 202311356741.9

(51) Int. Cl.
*C12N 7/00* (2006.01)
*C12N 5/071* (2010.01)

(52) U.S. Cl.
CPC ............. *C12N 7/00* (2013.01); *C12N 5/0686* (2013.01); *C12N 2500/90* (2013.01); *C12N 2710/16752* (2013.01); *C12N 2750/14352* (2013.01); *C12N 2770/16052* (2013.01)

(58) Field of Classification Search
CPC .... C12N 7/00; C12N 5/0686; C12N 2500/90; C12N 2710/16752; C12N 2750/14352; C12N 2770/16052
See application file for complete search history.

(56) References Cited

FOREIGN PATENT DOCUMENTS

| CN | 107299078 A | * | 10/2017 | .......... C12N 5/0686 |
| CN | 114107170 A | * | 3/2022 | |

OTHER PUBLICATIONS

Crandell et al (1973). Development, characterization, and viral susceptibility of a feline (Felis catus) renal cell line (CRFK). In Vitro. Nov.-Dec, 1973;9(3):176-85. (Year: 1973).*
Lawson et al (2019). Characterization of Crandell-Rees Feline Kidney (CRFK) cells as mesenchymal in phenotype. Research in Veterinary Science. 127 (2019) 99-102. (Year: 2019).*
Shimode et al (2022). Establishment of CRFK cells for vaccine production by inactivating endogenous retrovirus with TALEN technology. Sci Rep. Apr. 27, 2022;12(1):6641. (Year: 2022).*
ATCC (2022) Online product catalogue for CRFK CCL-94™. See webpage at : atcc.org/products/ccl-94 See attached pdf printout and see p. # 6 for thee priority date Dec. 4, 2022. (Year: 2022).*
Notice of Allowance of counterpart Chinese Patent Application No. 202311356741.9 issued on May 11, 2024.
Supplementary Search report of counterpart Chinese Patent Application No. 202311356741.9 issued on Sep. 12, 2023.
3305 Foreign virus test method, 3306 Sterility test or pure test method, 3307 Mbacterial count and pathogen identification, 3308 mycoplasma test, 3309 Avian adenovirus group I test, Appendix 25-36.

* cited by examiner

*Primary Examiner* — Nicole Kinsey White
*Assistant Examiner* — Samadhan Jaising Jadhao

(57) ABSTRACT

Provided are establishment and suspension acclimation of a Crandell Reese Feline Kidney (CRFK) adherent cell line, and its application. The CRFK cell line, named CRFK-BLA, is deposited at the China General Microbiological Culture Collection Center (CGMCC), with the address being Institute of Microbiology, Chinese Academy of Sciences, No. 3, Yard No. 1, Beichen West Road, Chaoyang District, Beijing, the deposit number being CGMCC NO: 45703; the CRFK cell line was classified and named CRFK cells, and was deposited on Aug. 17, 2023. A serum-free complete suspension culture type CRFK cell line obtained by acclimation on the basis of CRFK-BLA is named CRFK-BLS, and is deposited at the China General Microbiological Culture Collection Center (CGMCC), with the address being Institute of Microbiology, Chinese Academy of Sciences, No. 3, Yard No. 1, Beichen West Road, Chaoyang District, Beijing, the deposit number being CGMCC NO: 45704; the CRFK cell line was classified and named CRFK suspension cells.

4 Claims, 5 Drawing Sheets

A

B

A  B

ESTABLISHMENT AND SUSPENSION ACCLIMATION OF CRFK ADHERENT CELL LINE, AND ITS APPLICATION

CROSS-REFERENCE TO RELATED APPLICATION

The present application claims priority from Chinese Patent Application No. 202311356741.9 filed on Oct. 19, 2023, the contents of which are incorporated herein by reference in their entirety.

TECHNICAL FIELD

The present disclosure herein relates to the field of biotechnology, and more specifically, relates to establishment and suspension acclimation of a Crandell Reese Feline Kidney (CRFK) adherent cell line, and its application.

BACKGROUND

As the pet industry continues to expand, the number of pets being kept, predominantly cats and dogs, has been increasing annually. While pets bring joy to people's lives, pet health issues also pose a threat to public security. Currently, there is a limited number of commercialized pet vaccines available from animal vaccine enterprises in China, with varying quality levels. Most of these vaccines rely heavily on imports, resulting in high prices. Many enterprises and public institutions in China are now embarking on developing products in this field. Currently, among the viruses that harm pet cats, the primary ones include feline parvovirus, canine parvovirus, feline coronavirus, feline herpesvirus, etc. However, the virus that poses a significant threat to pet cats is feline parvovirus.

Traditional CRFK cell culture mostly adopts the method of serum-based adherent culture. Serum is a complex mixture formed by removing fibrin from plasma, which contains growth factors, hormones, carrier proteins, anchoring factors, trace elements and other nutrients essential for cell growth, and can effectively promote cell growth and product expression. However, there are also many problems in the application of serum: it is susceptible to contamination by viruses, *mycoplasma* or other pathogens; inter-batch differences make it difficult to strictly control the quality of products in different batches; the presence of a large amount of serum proteins results in an increment in the difficulty of downstream separation and purification, and some proteins are difficult to completely remove by means of separation and purification, which affects the final product quality; and in addition, serum is difficult to obtain and expensive, and the use of serum in large-scale animal cell culture will increase production costs. Both CRFK and F81 belong to epithelioid feline kidney cell lines. CRFK was first separated out by Crandell in 1964. F81 is an engineered cell line derived from CRFK through passage cloning and screening. Both CRFK and F81 cells are suitable for adherent culture, are more sensitive to a variety of pet viruses and endemic economic animal viruses, and thus have been widely used in research on veterinary biological products. For example, they are applied to canine parvovirus (CPV), feline panleukopenia virus (FPV), feline herpesvirus (FHV), feline calicivirus (FCV), mink viral enteritis virus (MEV), and the like.

In view of the inconsistent sensitivities of feline viral antigens (such as FPV, FHV, and FCV) on the conventional CRFK and F81 cell lines, polyvalent pet vaccines cannot be produced with a single cell line. In order to facilitate laboratory research and process development, the isolation of feline kidney primary cells and the establishment of continuous cell lines were studied; and CRFK cell lines that were more sensitive to pet viruses were selected. Two-dimensional single-cell layer adherent culture is basically adopted to culture CRFK cells. In a single-cell layer culture system, cell proliferation is easily limited by the surface area of the matrix, making it difficult to achieve large-scale production; and the digestion process will also increase the process complexity, production time and cost. However, single-cell suspension culture may be not limited by the cell growth surface, making it easy to achieve the large-scale production of cells and products. There is not much research work on CRFK cell culture methods, metabolic characteristics and culture processes. Therefore, the development and research of a serum-free single-cell suspension culture system for CRFK cells are of a great significance to its industrialization process.

SUMMARY

In order to solve the above technical problems, this study selected the kidneys of 10 days old kittens without specific pathogens, which were digested and ground before being cultured in a DMEM medium containing 10% fetal bovine serum. The stability of cell passage was verified through continuous screening and passage. After testing for exogenous viruses and *mycoplasma*, a CRFK cell line seed bank was established. The results showed that after 10 consecutive generations of screening and culture, the isolated feline kidney primary cells had basically the same cell morphology; after continuous passage to 45 generations, the cell morphology was single and the growth rate was stable, and the test for exogenous viruses and *mycoplasma* passed; a CRFK continuous cell line was successfully established, named CRFK, which was epithelial cell-like, belonging to a spontaneous immortal cell line. On this basis, serum-free acclimation was successfully carried out in a serum-free medium, and a CRFK-S cell strain suitable for serum-free single-cell suspension culture was obtained by a single-cell suspension culture acclimation method. It lays the foundation for the optimization and amplification of CRFK cell culture and virus vaccine amplification processes, and also provides reference for the culture processes of other animal cells and the industrial production of vaccines and other biological products.

Specifically, the present disclosure provides a CRFK cell line, which is named CRFK-BLA, and is deposited at the China General Microbiological Culture Collection Center (CGMCC), with the address being Institute of Microbiology, Chinese Academy of Sciences, No. 3, Yard No. 1, Beichen West Road, Chaoyang District, Beijing, and the deposit number being CGMCC NO: 45703; and the CRFK cell line was classified and named CRFK cells, and was deposited on Aug. 17, 2023.

Further, the present disclosure provides a serum-free acclimation method for CRFK cells, including the following steps:
  preparation of CRFK cells: inoculating the resuscitated CRFK cells (a deposited strain of CRFK-BLA) into a DMEM medium containing 8% fetal bovine serum, and subculturing for 5 generations according to the conventional method;
  gradient descent serum culture of CRFK cells: culturing the obtained adherent culture type CRFK cells in each of DMEM mediums containing 6%, 4%, and 2% fetal bovine serum in sequence for 6 generations, subculturing at a ratio of 1:3, and incubating at 37° C. in a cell incubator containing 5% $CO_2$;

low-serum adherent culture of CRFK cells in complete suspension medium: carrying out adherent culture on the cells obtained in the last generation in the previous step by using a complete suspension medium containing 2% fetal bovine serum; after the cells adhere to the wall and the monolayer confluent degree in a culture flask reaches 90% or more, discarding culture medium; digesting and dispersing with 0.125% EDTA-trypsin, subculturing in a ratio of 1:2, and incubating at 37° C. in a cell incubator containing 5% $CO_2$; carrying out continuous passage culture for 5 generations to obtain a low-serum adherent culture type CRFK cell line adapted to the complete suspension medium; and low-serum suspension culture of CRFK cells in complete suspension medium: adjusting the cell density obtained in the last generation in the previous step to $1\times10^6$ cells/mL by using a complete suspension medium containing 2% fetal bovine serum, and incubating at 37° C. and 120 r/min in a shaker containing 5% $CO_2$; when the cell density reaches $4\times10^6$ cells/mL, using a complete suspension medium containing 1% fetal bovine serum to culture the cells in flasks in a ratio of 1:4; when the cell density reaches $4\times10^6$ cells/mL, using a complete suspension medium containing 0.5% fetal bovine serum to culture the cells in flasks in a ratio of 1:3; after five consecutive passages, performing acclimation to obtain a low-serum complete suspension culture type CRFK cell line; and incubating at 37° C. and 120 r/min in a shaker containing 5% $CO_2$, and performing acclimation to obtain a low-serum complete suspension culture type CRFK cell line.

Further, the present disclosure provides a serum-free acclimation method for CRFK single-cell suspension, including the following steps:

single-cell screening using a 96-well plate: centrifuging the low-serum complete suspension culture type CRFK cell line, and then adding same into a serum-free complete suspension medium; blowing the suspended cells and counting, diluting the cells with the serum-free complete suspension medium so as to prepare 10 cells/mL cell suspension; adding the cell suspension into a 96-well cell culture plate at 100 μl/well, and incubating at 37° C. in a cell incubator containing 5% $CO_2$;

single-cell screening using a 24-well plate: culturing for 48-72 h, selecting several culture wells with only 1 cell/well from the 96-well cell culture plate, and selecting the single cell lines that grow well; transferring them to a 24-well plate, and incubating at 37° C. in a cell incubator containing 5% $CO_2$;

single-cell screening using a 6-well plate: culturing for 48-72 h, selecting the single cell lines that grow well from the 24-well cell culture plate; transferring them to a 6-well plate, and incubating at 37° C. in a cell incubator containing 5% $CO_2$;

single-cell adherent amplification culture: culturing for 48-72 h, selecting the single cell lines that grow well from the 6-well cell culture plate; transferring them to a 25 $cm^2$ culture flask, and incubating at 37° C. in a cell incubator containing 5% $CO_2$; and single-cell suspension culture: when the cells grow to 90%, digesting them according to the above method, and then transferring them to a shake flask to continue culturing; and adjusting the cell density to $5\times10^5$ cells/mL, incubating at 37° C. and 120 r/min in a shaker containing 5% $CO_2$, and performing acclimation to obtain a serum-free complete suspension culture type CRFK cell line.

Further, the present disclosure provides a serum-free complete suspension culture type CRFK cell line, which is named CRFK-BLS, and is deposited at the China General Microbiological Culture Collection Center (CGMCC), with the address being Institute of Microbiology, Chinese Academy of Sciences, No. 3, Yard No. 1, Beichen West Road, Chaoyang District, Beijing, and the deposit number being CGMCC NO: 45704; and the CRFK cell line was classified and named CRFK suspension cells, and was deposited on Aug. 17, 2023.

Further, the present disclosure provides an application of the CRFK cell line and/or the serum-free complete suspension culture type CRFK cell line in any one of (1) to (8):
(1) virus cultivation;
(2) preparation of products for culturing viruses;
(3) virus isolation;
(4) preparation of products for isolating viruses;
(5) virus detection for non-diagnostic and non-therapeutic purposes;
(6) preparation of products for detecting viruses;
(7) preparation of virus vaccines; and
(8) drug screening.

The viruses include canine parvovirus, feline panleukopenia virus, feline calicivirus, feline infectious rhinotracheitis virus, and mink viral enteritis virus.

The drugs are used for preventing or treating diseases caused by viral infections.

The present disclosure further provides a method for culturing virus vaccines using the aforementioned CRFK cell line and/or the serum-free complete suspension culture type CRFK cell line.

DETAILED DESCRIPTION OF THE EMBODIMENTS

Figure 1:
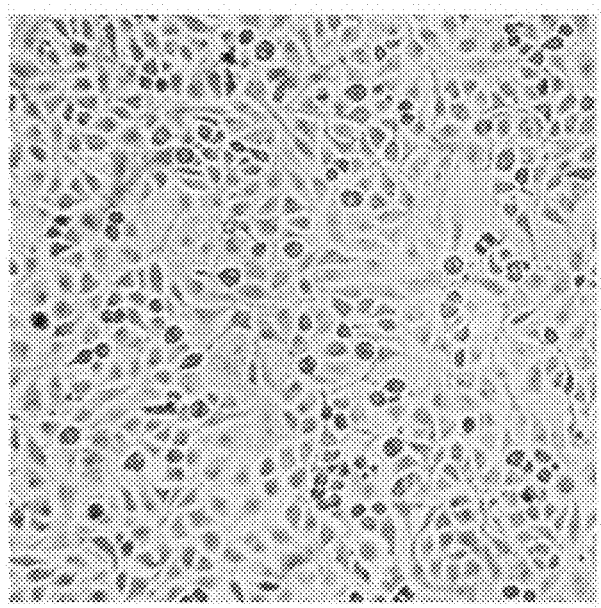
FIG. 1 shows the F10 generation (20×) of feline kidney primary cells.

The following are specific embodiments of the present disclosure to further illustrate the present disclosure, but should not be construed as limiting the scope of the present disclosure. Those skilled in the art should understand that the details and forms of the technical solutions of the present disclosure can be modified or replaced without departing from the spirit and scope of the present disclosure, but these modifications or replacements shall all fall within the protection scope of the present disclosure.

The experimental methods used in the following embodiments are conventional methods unless otherwise specified. Main Biological Materials and Equipment Involved in Experiments The virus species, including feline parvovirus HBX05 strain, feline herpesvirus BJS01 strain and feline calicivirus BJH13 strain, were isolated, identified and deposited by Taizhou Bioally Technology Co., Ltd.

Experimental animals: 10 days old female kittens without specific pathogens (negative for FPV, FHV, and FCV antigen tests).

Main reagents: viral genomic DNA/RNA extraction kit and RNA reverse transcription kit, purchased from Beijing TransGen Biotechnology Co., Ltd.; PCR and RT-PCR amplification kits, purchased from TaKaRa Bioengineering (Dalian) Co., Ltd.; thioglycolate fluid medium (TG), trypticase soy broth (TSB), *mycoplasma* liquid medium, and *mycoplasma* solid medium, purchased from Beijing Zhonghai Biotechnology Co., Ltd.; and high-glucose DMEM medium (ME105-001) and special-grade South American fetal bovine serum (S711-001S), purchased from Suzhou ShuangRu Biotechnology Co., Ltd.

A serum-free medium was prepared based on a DMEM medium by adding insulin, transferrin, cholesterol, sodium bicarbonate, HEPES, Pluronic F68 and other components (see the table below for specific components), and was filtered and sterilized through a 0.1 μm microporous filter membrane.

| Components | Content (mg/L) |
|---|---|
| L-asparagine monohydrate | 750 |
| L-isoleucine | 400 |
| L-phenylalanine | 300 |
| L-glutamic acid | 300 |
| L-threonine | 350 |
| L-cysteine hydrochloride monohydrate | 350 |
| L-lysine hydrochloride | 500 |
| L-proline | 400 |
| L-serine | 700 |
| L-arginine hydrochloride | 350 |
| L-histidine hydrochloride monohydrate | 250 |
| L-methionine | 200 |
| L-valine | 400 |
| L-aspartic acid | 1500 |
| L-leucine | 700 |
| L-tyrosine disodium salt hydrate | 250 |
| L-tryptophan | 200 |
| L-ascorbate 2-phosphate hemimagnesium salt hydrate | 15 |
| Choline chloride | 80 |
| Inositol | 60 |
| Para aminobenzoic acid | 1.5 |
| Vitamin B12 | 50 |
| D-calcium pantothenate | 6 |
| Nicotinamide | 80 |
| Pyridoxine hydrochloride | 32 |
| Vitamin b1 hydrochloride | 12 |
| D-biotin | 1.5 |
| Folic acid | 25 |
| Riboflavin | 1 |
| Ethylenediaminetetraacetic acid tetrasodium salt tetrahydrate | 2.5 |
| Ferrous sulfate heptahydrate | 2 |
| 2-hydroxypyridine nitrogen oxide | 1.5 |
| Anhydrous calcium chloride | 10 |
| Magnesium chloride hexahydrate | 170.66107 |
| Zinc sulfate heptahydrate | 3 |
| Reduced glutathione | 0.6 |
| Thioglycerol | 6 |
| Alpha-lipoic acid | 1.3 |
| Linoleic acid | 0.04 |
| D-glucose | 6000 |
| Hydroxyethyl piperazine ethylsulfonic acid (HEPES) | 2000 |
| Sodium bicarbonate | 2300 |
| Sodium pyruvate | 140 |
| Potassium chloride | 400 |
| Anhydrous disodium hydrogen phosphate | 500 |
| Sodium dihydrogen phosphate monohydrate | 172.5 |
| Phenol red | 2 |

Embodiment 1: Establishment of CRFK-BLA Cell Line

Isolation and culture of feline kidney primary cells: the screened kittens without specific pathogens were painlessly euthanized and then soaked in a 75% alcohol solution; the abdominal cavity was cut open in a biosafety cabinet for taking out the kidneys, and the fascial layer of renal tissue was exfoliated; the obtained kidneys were cut into the size of rice grains with sterile scissors, and then rinsed for 3 times with sterile PBS buffer; 20 ml of trypsin with a concentration of 0.5 mg/ml was added, and the obtained mixture was placed in a constant temperature incubator at 37° C. for digestion for 1 h; the product was ground with a sterile grinder, and cell suspension was filtered with a 100-mesh screen; centrifugation was performed at 700 r/min for 5 min, and the product was washed for three times with a complete medium (DMEM containing 10% fetal bovine serum); and after being resuspended in 10 ml of the complete medium, the product was cultured at 37° C. in a constant temperature incubator containing 5% $CO_2$, which was denoted as F1.

After being cultured for 24 h, the primary cells were washed for 3 times with preheated PBS and then transferred into a new complete medium for culturing; after a monolayer was fully grown, the cells were rinsed with 0.125% trypsin to flush out cells in poor conditions; after culture medium was discarded, 0.125% trypsin was added again for digestion; and after being observed under a microscope to disperse into single cells, the cells were added into a complete medium immediately and passaged at a ratio of 1:3. Culturing was continued in this way until F10. After 10 consecutive generations of isolation and culture, the feline kidney primary cells were in good conditions. The feline kidney primary cells from the generation F10 that had grown well to a monolayer were observed under a microscope. The cells are rhombus-shaped and oblong-shaped, and have clear outlines (see FIG. 1).

Figure 2:
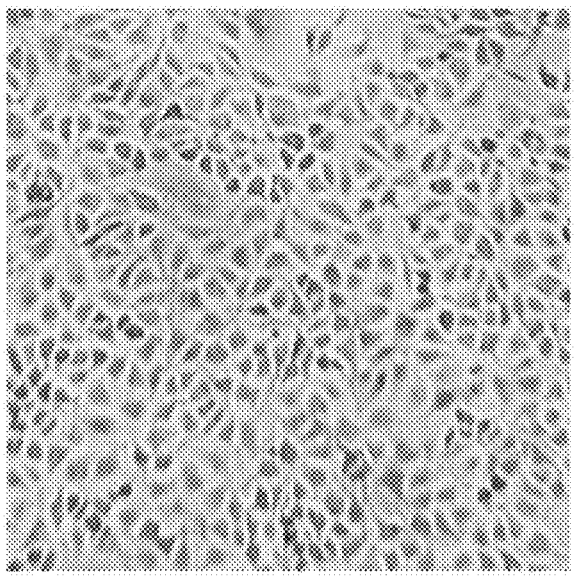
FIG. 2 shows a CRFK cell line at different generations (20×), where A of FIG. 2 represents CRFK-F15 (15th generation); and B of FIG. 2 represents CRFK-F20 (20th generation).
Figure 2:
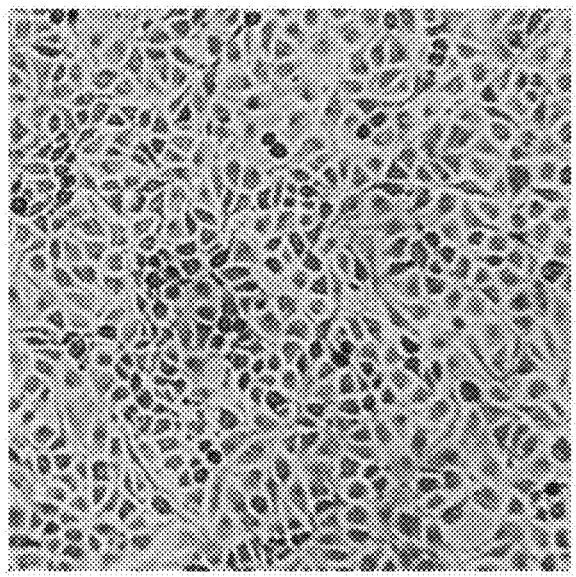

The monolayer feline kidney primary cells in good conditions were taken and rinsed with 0.125% trypsin; after culture medium was discarded, 0.125% trypsin was added again for digestion; after being observed under a microscope to disperse into single cells, the cells were added into a complete medium immediately and passaged at a ratio of 1:3; and the product was cultured at 37° C. in a cell incubator containing 5% $CO_2$. Passage was carried out continuously to F45 according to the above method, and the cell morphology and status were observed. The cell morphology of each passage was normal, and was rhombus-shaped and oblong-shaped, with clear outline (see FIG. 2); and the cell growth rate was stable. It shows that the feline kidney primary cells may be used as a continuous cell line after being subjected to continuous screening and culture. They are named CRFK-BLA and belong to a spontaneous permanent cell line.

The monolayer feline kidney primary cells in good conditions were taken and rinsed with 0.125% trypsin; after culture medium was discarded, 0.125% trypsin was added again for digestion; after being observed under a microscope to disperse into single cells, the cells were added into a complete medium immediately to prepare cell suspension for counting; centrifugation was performed at 800 r/min for 8-10 min, the supernatant was discarded, cryoprotectant (DMEM: fetal bovine serum: DMSO=6:3:1) was added, the obtained mixture was gently blown and evenly mixed, and the cell concentration was adjusted to $2.0 \times 10^6$/ml; and the product was transferred into cryopreservation tubes, with 1.0 ml for each tube, and then labeled and stored in liquid nitrogen for later use.

CRFK-BLA Cell Line Purity Test

Cell resuscitation: CRFK-BLA cells frozen in liquid nitrogen were taken out, then placed in a water bath at 37° C. to thaw rapidly, and centrifuged at 800 r/min for 8-10 min. The obtained cells were added into a complete serum medium, gently blown to resuspend, and then transferred into a T25 cell flask; and the product was cultured at 37° C. in a cell incubator containing 5% $CO_2$.

Sterility test: CRFK-BLA cells were taken and tested according to Appendix 3306, Volume III, Chinese Veterinary Pharmacopoeia, 2020 edition.

*Mycoplasma* test: CRFK-BLA cells were taken and tested according to Appendix 3308, Volume III, Chinese Veterinary Pharmacopoeia, 2020 edition.

Exogenous virus test: CRFK-BLA cells were taken and tested according to Appendix 3305, Volume III, Chinese Veterinary Pharmacopoeia, 2020 edition.

After resuscitation, the CRFK-BLA cell bank cells F10, F20 and F30 were tested for purity. All passages of cells passed the test and were free of bacteria, *mycoplasma* and exogenous virus contamination.

After the cells F20 were isolated, purified and amplified, they were named CRFK-BLA and deposited at the China General Microbiological Culture Collection Center (CGMCC), with the address being Institute of Microbiology, Chinese Academy of Sciences, No. 3, Yard No. 1, Beichen West Road, Chaoyang District, Beijing, and the deposit number being CGMCC NO: 45703; and the cells were classified and named CRFK cells, and were deposited on Aug. 17, 2023.

Embodiment 2: Virus Sensitivity Test for CRFK-BLA Cell Line

Figure 3:
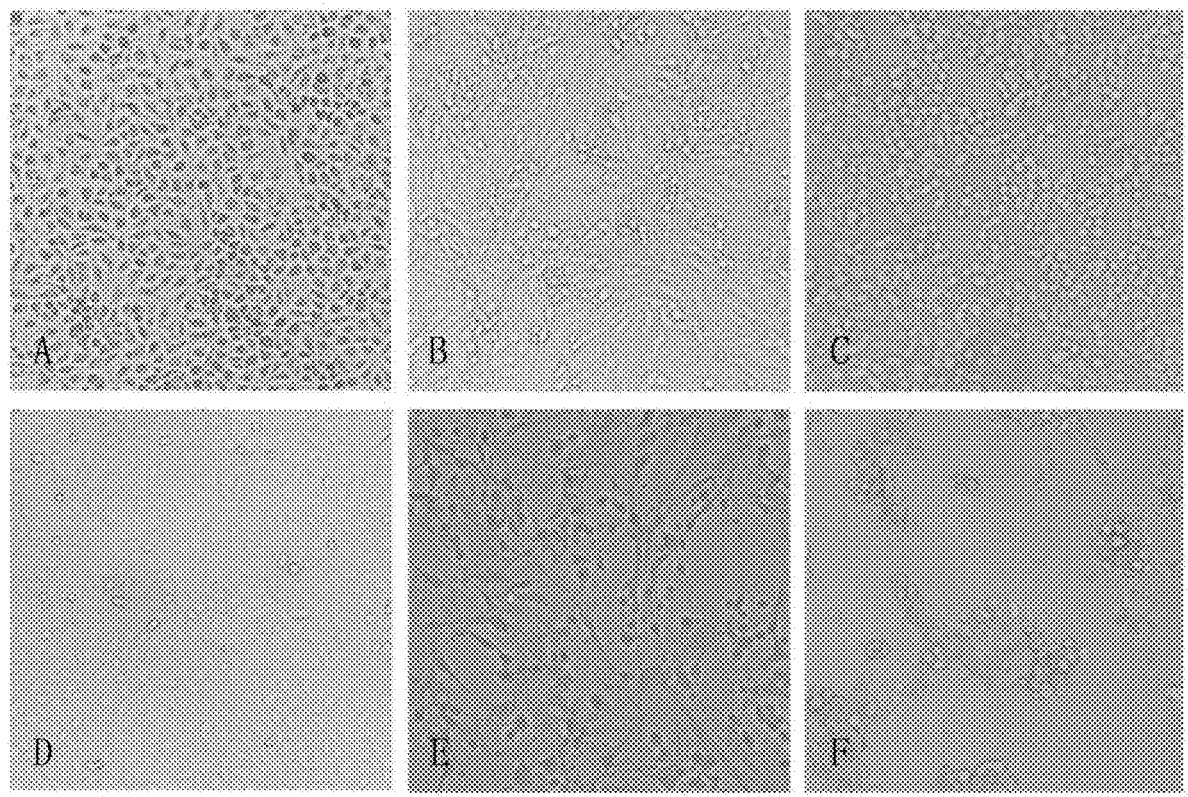
FIG. 3 shows a virus culture sensitivity experiment (20×) of a CRFK cell line, where A of FIG. 3 represents a CRFK-BLA control, B of FIG. 3 represents CRFK-BLA-FPV, C of FIG. 3 represents CRFK-BLA-FHV, D of FIG. 3 represents a CRFK control, E of FIG. 3 represents CRFK-FPV, and F of FIG. 3 represents CRFK-FHV.
Figure 4:
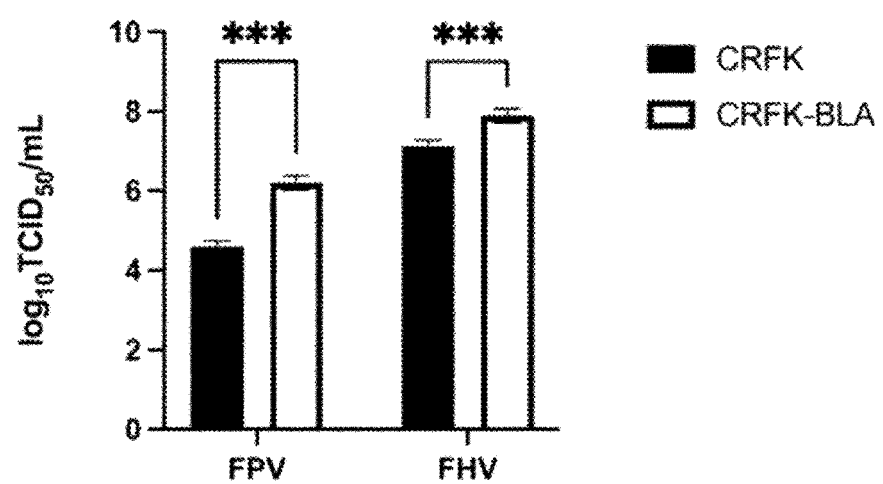
FIG. 4 shows viral titers of CRFK and CRFK-BLA.

Feline parvovirus (HBX05 strain), feline herpesvirus (BJS01 strain) and feline calicivirus (BJH13 strain) were respectively inoculated into CRFK cells and deposited strain CRFK-BLA cells in T25 cell bottles according to a volume ratio: (①) FPV: simultaneous inoculation, inoculated into 10 ml of CRFK cell suspension containing 2% bovine serum at a ratio of 5%; (②) FHV: inoculated into CRFK cells that have grown into a monolayer at a ratio of 0.1%; (③) FCV: inoculated into CRFK cells that have grown into a monolayer at a ratio of 0.1%); at the same time, normal cells were used as a control; and the cells were placed at 37° C. in an incubator containing 5% $CO_2$ for culture and observation. Whether the CRFK-BLA cell line was sensitive to all virus strains was observed; and when the cytopathic lesions reached 80%, the virus liquid was collected and enabled to be subjected to freeze thawing for three times, and then the virus $TCID_{50}$ was determined. The results showed that obvious cytopathic lesions were seen after CRFK-BLA cells were exposed to the virus (see FIG. 3). After simultaneous inoculation of the FPV HBX05 strain, the typical lesions, such as swelling, rounding and drawing of cells, could be observed under a microscope. After inoculation of the FHVBJS01 strain, the cells showed round shrinkage and shedding lesions under a microscope. After inoculation of the FCV BJH13 strain, the typical lesions, such as cell agglomeration, shedding and grape clustering, could be observed under a microscope. The virus titers of the viruses cultured with the CRFK-BLA were higher than those of the viruses cultured with the CRFK cells (FIG. 4).

Embodiment 3: Serum-Free Acclimation of CRFK-BLA Cell Line

The serum content in a medium was reduced by the gradient of a stepwise adaptation method.

Preparation of CRFK cells: inoculating the resuscitated CRFK cells (a deposited strain of CRFK-BLA) into a DMEM medium containing 8% fetal bovine serum, and DMEM was used as a base medium, with 8% fetal bovine serum being added for incubation (pH value: 6.8-7.2); and the product was incubated at 37° C. in a cell incubator containing 5% $CO_2$. After the cells adhered to the wall and the monolayer confluent degree in a culture flask reached 90% or more, culture medium was discarded, and the product was digested and dispersed with 0.125% EDTA-trypsin, and then was subcultured for 5 generations according to the conventional method.

Gradient descent serum culture of CRFK cells: the obtained adherent culture type CRFK cells were cultured in each of DMEM mediums containing 6%, 4%, and 2% fetal bovine serum in sequence for 6 generations, subcultured at a ratio of 1:3, and then incubated at 37° C. in a cell incubator containing 5% $CO_2$.

Low-serum adherent culture of CRFK cells in complete suspension medium: adherent culture was carried out on the cells obtained in the last generation in the previous step by using a complete suspension medium (as described in the above formula) containing 2% fetal bovine serum; after the cells adhered to the wall and the monolayer confluent degree in a culture flask reached 90% or more, culture medium was discarded; the product was digested and dispersed with 0.125% EDTA-trypsin, subcultured in a ratio of 1:2, and incubated at 37° C. in a cell incubator containing 5% $CO_2$; and continuous passage culture was carried out for 5 generations to obtain a low-serum adherent culture type CRFK cell line adapted to the complete suspension medium.

Low-serum suspension culture of CRFK cells in complete suspension medium: the cell density obtained in the last generation in the previous step was adjusted to $1 \times 10^6$ cells/mL by using a complete suspension medium containing 2% fetal bovine serum, and the cells were incubated at 37° C. and 120 r/min in a shaker containing 5% $CO_2$; when the cell density reached $4 \times 10^6$ cells/mL, a complete suspension medium containing 1% fetal bovine serum was used to culture the cells in flasks in a ratio of 1:4; when the cell density reached $4 \times 10^6$ cells/mL, a complete suspension medium containing 0.5% fetal bovine serum was used to culture the cells in flasks in a ratio of 1:3; after five consecutive passages, acclimation was performed to obtain a low-serum complete suspension culture type CRFK cell line; and the obtained cell line was incubated at 37° C. and 120 r/min in a shaker containing 5% $CO_2$.

Figure 5:
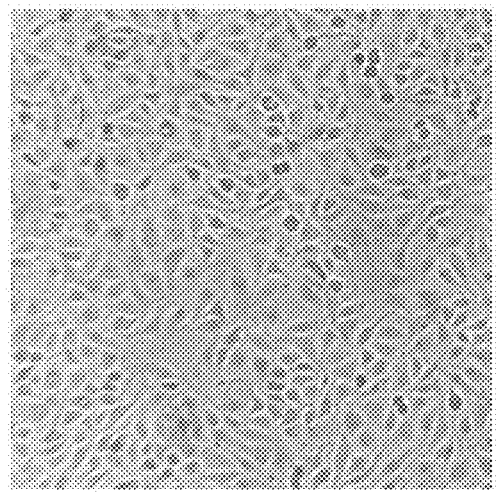
FIG. 5 shows the results of low-serum and suspension acclimation of a CRFK cell line (20×), where A of FIG. 5 represents the adherent growth of CRFK-BLA in 2% FBS and DMEM, and B of FIG. 5 represents the suspension growth of CRFK-BLA in 0.5% FBS and complete suspension medium.
Figure 5:
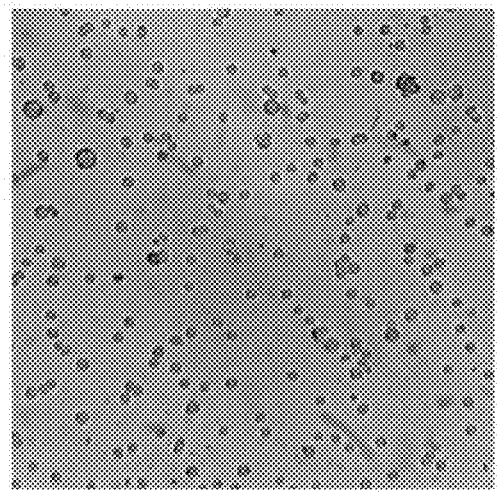

After continuous gradient serum reduction, the self-isolated CRFK-BLA cell line was able to normally grow adhering to the wall and passage in the DMEM medium containing 2% fetal bovine serum (see A of FIG. 5). The cell morphology of each passage was normal, and was rhombus-shaped and oblong-shaped, with clear outlines. After being suspended and acclimated in the low-serum complete suspension medium, the CRFK-BLA cell line could grow normally in the complete suspension medium containing 0.5% fetal bovine serum (see B of FIG. 5). Under a microscope, it appeared single and transparent, with clear cell outline and high transparency. It shows that the low-serum complete suspension culture type CRFK-BLA cell line can be obtained through acclimation.

Embodiment 4: Acclimation Method for CRFK-BLA Single-Cell Suspension

Single-cell screening using a 96-well plate: the low-serum complete suspension culture type CRFK-BLA cell line was centrifuged, and then added into a serum-free complete suspension medium (as described in the above formula); the suspended cells were blown and counted, and the cells were diluted with the serum-free complete suspension medium so as to prepare 10 cells/mL cell suspension; and the cell suspension was added into a 96-well cell culture plate at 100 μl/well, and then incubated at 37° C. in a cell incubator containing 5% $CO_2$.

Single-cell screening using a 24-well plate: the cells were cultured for 48-72 h, several culture wells with only 1 cell/well were selected from the 96-well cell culture plate, and the single cell lines that grow well were selected; and the selected cell lines were transferred to a 24-well plate, and then incubated at 37° C. in a cell incubator containing 5% $CO_2$.

Single-cell screening using a 6-well plate: the cells were culturing for 48-72 h, and the single cell lines that grow well were selected from the 24-well cell culture plate; and the selected cell lines were transferred to a 6-well plate, and then incubated at 37° C. in a cell incubator containing 5% $CO_2$.

Single-cell adherent amplification culture: the cells were cultured for 48-72 h, and the single cell lines that grow well were selected from the 6-well cell culture plate; and the selected cell lines were transferred to a 25 $cm^2$ culture flask, and then incubated at 37° C. in a cell incubator containing 5% $CO_2$.

Figure 6:
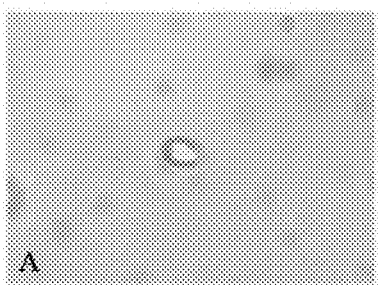
FIG. 6 shows the process of cell growth from monoclonal to monolayer, where A of FIG. 6 represents serum-free acclimation monoclonal CRFK-BLA, B of FIG. 6 represents single-cell proliferate into two cells through mitosis, C of FIG. 6 represents two cells proliferate into four cells through mitosis, D of FIG. 6 represents four cells divide into eight cells, E of FIG. 6 represents cells spread and proliferate on the matrix, and F of FIG. 6 represents single-cell form a continuous single-layer cell.
Figure 6:
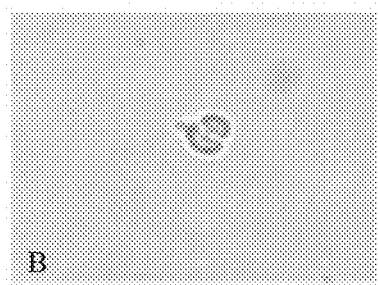
Figure 6:
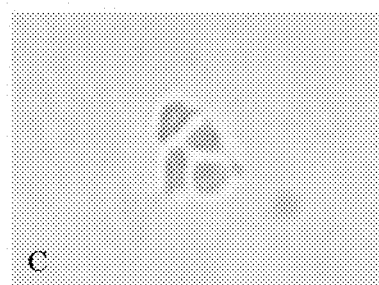
Figure 6:
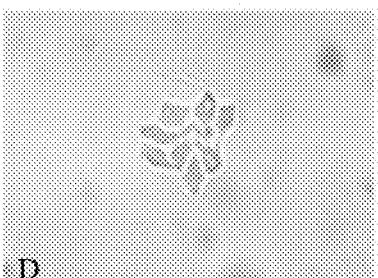
Figure 6:
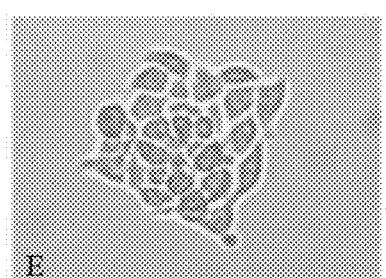
Figure 6:
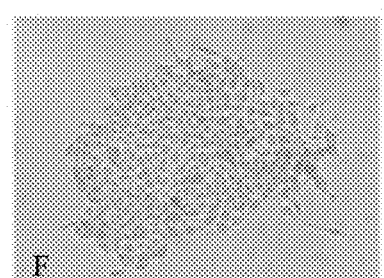
Figure 7:
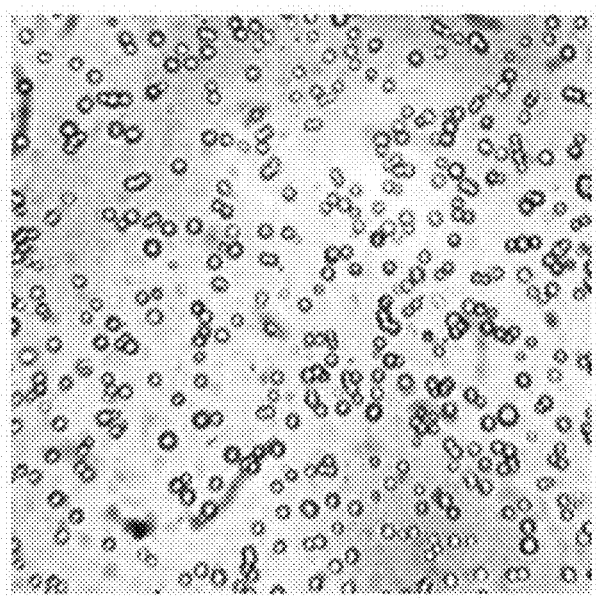
FIG. 7 shows the microscopic results (20×) of a suspended CRFK-BLS cell line.

Single-cell suspension culture: when the cells grew to 90%, the cells were digested according to the above method, and then transferred to a shake flask to continue culturing. The cell density was adjusted to $5 \times 10^5$ cells/mL, the cells were then incubated at 37° C. and 120 r/min in a shaker containing 5% $CO_2$, and acclimation was performed to obtain a serum-free complete suspension culture type CRFK cell line (see FIG. 6). This cell line could grow normally in the serum-free medium, with unchanged cell morphology and clear outline, taking on the shapes of rhombus and oblong. After being transferred to a shake flask for culturing, the CRFK cell line was subcultured at the density of $5 \times 10^5$ cells/mL, and was subjected to continuous passage culture in a serum-free medium for 5 generations. The CRFK cell line achieved normal suspension growth in the complete suspension medium (see FIG. 7). Under a microscope, it appeared single and transparent, with clear cell outline and high transparency, and was named CRFK-BLS.

After the serum-free complete suspension culture type CRFK cells obtained by acclimation were isolated, purified and amplified, they were named CRFK-BLS and deposited at the China General Microbiological Culture Collection Center (CGMCC), with the address being Institute of Microbiology, Chinese Academy of Sciences, No. 3, Yard No. 1, Beichen West Road, Chaoyang District, Beijing, and the deposit number being CGMCC NO: 45704; and the cells were classified and named CRFK suspension cells, and were deposited on Aug. 17, 2023.

Figure 8:
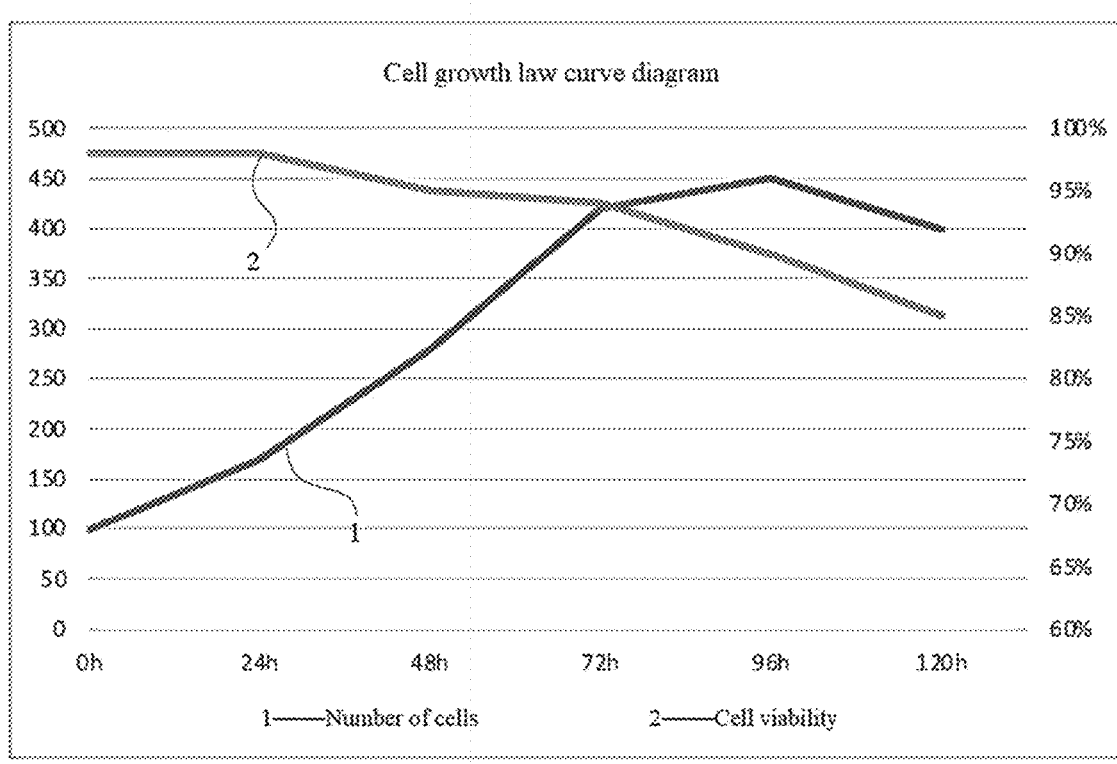
FIG. 8 shows the microscopic growth pattern of a suspended CRFK-BLS cell line.

The established CRFK-BLS cell line was passaged and subcultured at the density of $1 \times 10^6$ cells/mL, and was stained with trypan blue every 24 h; the numbers of dead cells and living cells were counted with a hemocytometer, and the cell viability was calculated and displayed (see FIG. 8); and after 96 h of suspension culture, the cells reached a maximum density of $4.5 \times 10^6$ cells/mL, with a viability of 90±0.5% and a doubling time of 25.37±0.35 h. It shows that the growth stability of this monoclonal cell line (CRFK-BLS) is better.

Figure 9:
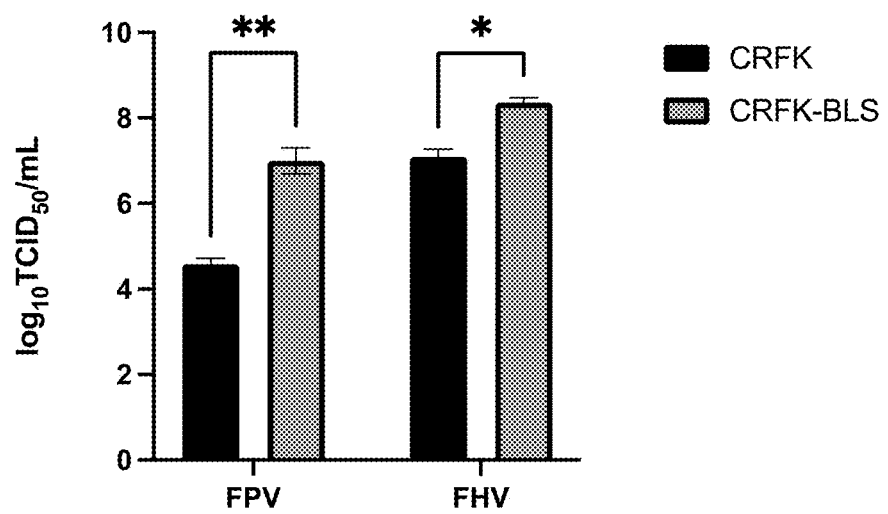
FIG. 9 shows a virus sensitivity experiment of a CRFK-BLS cell line.

Virus sensitivity test: the established CRFK-BLS cell line was passaged and subcultured at the density of $1 \times 10^6$ cells/mL. When the cell density reached $2.0 \times 10^6$ cells/mL, feline parvovirus (HBX05 strain), feline herpesvirus (BJS01 strain) and feline calicivirus (BJH13 strain) were inoculated into CRFK-BLS suspension culture shake flasks according to certain volume ratios (① FPV: inoculated at a ratio of 5%; ② FHV: inoculated at a ratio of 0.1%; ③ FCV: inoculated at a ratio of 0.1%); at the same time, normal cells were used as a control; and the cells were cultured at 37° C. and 120 r/min in a shaker containing 5% $CO_2$. Whether the CRFK-R cell line was sensitive to all virus strains was observed. Virus liquid was collected and enabled to be subjected to freeze thawing for 3 times, and then the virus $TCID_{50}$ (see FIG. 9) was determined. It is confirmed that this monoclonal cell line (CRFK-BLS) is more conducive to FPV and FHV culture than traditional adherent CRFK cells.

The foregoing description of the embodiments is provided to facilitate the understanding and use of the present disclosure by those of ordinary skill in the art. It will be apparent to those skilled in the art that various modifications can be readily made to these embodiments and that the general principles described herein can be applied to other embodiments without the need for creative labor. Therefore, the present disclosure is not limited to the above-described embodiments. According to the principle of the present disclosure, improvements and modifications made by those skilled in the art without departing from the scope of the present disclosure shall fall within the protection scope of the present disclosure.

What is claimed is:

1. A Crandell Reese Feline Kidney (CRFK) cell line, wherein the CRFK cell line, named CRFK-BLA, is deposited at the China General Microbiological Culture Collection Center (CGMCC), with the address being Institute of Microbiology, Chinese Academy of Sciences, No. 3, Yard No. 1, Beichen West Road, Chaoyang District, Beijing, and the deposit number being CGMCC NO: 45703; and the CRFK cell line was classified and named CRFK cells, and was deposited on Aug. 17, 2023.

2. A serum-free complete suspension culture type CRFK cell line, wherein the serum-free complete suspension culture type CRFK cell line, named CRFK-BLS, is deposited at the China General Microbiological Culture Collection Center (CGMCC), with the address being Institute of Microbiology, Chinese Academy of Sciences, No. 3, Yard No. 1, Beichen West Road, Chaoyang District, Beijing, and the deposit number being CGMCC NO: 45704; and the CRFK cell line was classified and named CRFK suspension cells, and was deposited on Aug. 17, 2023.

3. A method for culturing virus vaccines using the CRFK cell line according to claim 1, the virus is selected from the group consisting of canine parvovirus, feline panleukopenia virus, feline calicivirus, feline infectious rhinotracheitis virus, and mink viral enteritis virus.

4. A method for culturing virus vaccines using the serum-free complete suspension culture type CRFK cell line according to claim 2, the virus is selected from the group consisting of canine parvovirus, feline panleukopenia virus, feline calicivirus, feline infectious rhinotracheitis virus, and mink viral enteritis virus.

\* \* \* \* \*